United States Patent
Fosshode et al.

(10) Patent No.: US 12,426,580 B2
(45) Date of Patent: Sep. 30, 2025

(54) SYSTEM FOR POLYCHAETE PRODUCTION COMPRISING A RETRIEVABLE TRAY, AND METHOD FOR POLYCHAETE PRODUCTION

(71) Applicant: Marine Bio Solutions AS, Trondheim (NO)

(72) Inventors: John Arnold Fosshode, Trondheim (NO); Marianne Larssen Langvik, Trondheim (NO); Svein Reppe, Trondheim (NO); Haavard Wollan, Trondheim (NO); Stein W. Österhus, Trondheim (NO)

(73) Assignee: Marine Bio Solutions AS, Trondheim (NO)

( * ) Notice: Subject to any disclaimer, the term of this patent is extended or adjusted under 35 U.S.C. 154(b) by 191 days.

(21) Appl. No.: 18/004,535

(22) PCT Filed: Jul. 7, 2021

(86) PCT No.: PCT/NO2021/050163
§ 371 (c)(1),
(2) Date: Jan. 6, 2023

(87) PCT Pub. No.: WO2022/010362
PCT Pub. Date: Jan. 13, 2022

(65) Prior Publication Data
US 2023/0240273 A1    Aug. 3, 2023

(30) Foreign Application Priority Data

Jul. 9, 2020 (NO) .................................. 20200806

(51) Int. Cl.
*A01K 67/362* (2025.01)
*A01K 67/30* (2025.01)

(52) U.S. Cl.
CPC ............ *A01K 67/30* (2025.01); *A01K 67/362* (2025.01)

(58) Field of Classification Search
None
See application file for complete search history.

(56) References Cited

U.S. PATENT DOCUMENTS 5,543,034 A * 8/1996 Hilbertz ................. A01K 61/50
                                                  204/DIG. 6
7,004,109 B2 * 2/2006 Olive ..................... A01K 67/30
                                                    119/6.7

(Continued)

FOREIGN PATENT DOCUMENTS

CN    1561714 A    1/2005
CN    104351112 A    2/2015

(Continued)

OTHER PUBLICATIONS

Merged translation of WO_2012022860 (Year: 2012).*

(Continued)

*Primary Examiner* — Morgan T Jordan
(74) *Attorney, Agent, or Firm* — Alix, Yale & Ristas, LLP (57) ABSTRACT

System for high-intensity polychaete production that includes at least two cultivation units and a feeding unit. Each cultivation unit being formed by a housing provided with at least one inlet at a first end thereof for supply of water and feed from the feeding unit and an outlet at a second end thereof for discharge of water and excess feed. At least one of the at least two cultivation units includes rows of trays arranged along a height direction of the housing, with the trays being retrievable from the housing. Each row of trays includes several trays arranged in series in a longitudinal direction of the cultivation unit with the housing enclosing, in the longitudinal direction, the series of (Continued)

trays arranged in said horizontal plane, with a spacing forming an inlet chamber and an outlet chamber at respective ends of the series of trays, with the inlet chamber being in fluid communication with the inlet and with the outlet chamber being in fluid communication with the outlet.

20 Claims, 7 Drawing Sheets

(56) References Cited

U.S. PATENT DOCUMENTS

| | | | |
|---|---|---|---|
| 7,156,048 B2 * | 1/2007 | Olive | A01K 67/30 119/6.7 |
| 7,568,446 B2 * | 8/2009 | Olive | A01K 67/30 119/6.7 |
| 2004/0159288 A1 * | 8/2004 | Olive | A01K 67/0332 119/6.7 |
| 2009/0050066 A1 * | 2/2009 | Aronowicz | A01K 61/17 119/200 |
| 2019/0059354 A1 * | 2/2019 | Tong | A01K 61/40 |

FOREIGN PATENT DOCUMENTS

| | | | | | |
|---|---|---|---|---|---|
| DE | 202017107283 U1 * | 4/2019 | | | A01G 33/00 |
| GB | 2349786 A | 11/2000 | | | |
| JP | 2019037148 A | 3/2019 | | | |
| KR | 20100002603 A | 1/2010 | | | |
| KR | 101170304 B1 * | 8/2012 | | | |
| KR | 101178392 B1 * | 8/2012 | | | |
| KR | 101191780 B1 | 10/2012 | | | |
| KR | 20140028218 A * | 3/2014 | | | |
| KR | 20140134826 A * | 11/2014 | | | |
| WO | 2010017172 A2 | 2/2010 | | | |
| WO | WO-2012022860 A1 * | 2/2012 | | | A01K 63/02 |
| WO | WO-2016012489 A1 * | 1/2016 | | | A01G 33/00 |

OTHER PUBLICATIONS

Merged translation of KR_101170304 (Year: 2012).*
Merged translation of KR_101178392 (Year: 2012).*
Merged translation of KR_20140028218 (Year: 2014).*
Merged translation of KR_20140134826 (Year: 2014).*
Merged translation of WO_2016012489 (Year: 2016).*
Merged translation of DE_202017107283 (Year: 2019).*
International Search Report and Written Opinion mailed on Sep. 16, 2021 for International Patent Application No. PCT/NO2021/050163.
International Preliminary Report on Patentability mailed on Oct. 20, 2022 for International Patent Application No. PCT/NO2021/050163.

* cited by examiner

SYSTEM FOR POLYCHAETE PRODUCTION COMPRISING A RETRIEVABLE TRAY, AND METHOD FOR POLYCHAETE PRODUCTION

BACKGROUND

The present invention is related to a system for high-intensity polychaete production and also related to a method for high-intensity polychaete production.

The animal farming industry continuously search for sustainable development solutions. Presently there are performed studies indicating that the use of polychaete in fish or other animal feed will be favourable due to their fatty acid composition and content of essential amino acid. Other uses of polychaete may include applications where polychaete can replace other, less sustainable, ingredients, such as cosmetics.

Presently, there exists no solutions of how to provide a large-scale polychaete production.

Further, there exists no solutions of how to provide a continuous polychaete production.

Further, there exists no solutions of how to provide high-intensity production of polychaete.

Further, there exists no solutions of how to provide high-intensity production of polychaete, and where such production accommodates farming of various species of polychaete.

Further, there exists no solutions of how to provide high-intensity production of polychaete, and where such production accommodates application of light, sound, temperature, water quality adjustments or polychaete farming feed in order to systematically influence a desired output of farmed polychaete.

It is further a need for production of marine proteins and fat. The present production is not sufficient to meet the need in the market.

There is also a need for production of feed close to production sites of, e.g., fish that requires large amounts of feed.

It is a need for production of polychaete for use in feed for other species/domestic animals.

Accordingly, there is a need for a system and method solving the above-mentioned lacks.

SUMMARY

Provided herein is a system and method for large-scale polychaete production.

Also provided herein is a system and method enabling continuous polychaete production.

Also provided herein is a system and method enabling high-intensity polychaete production.

Also provided herein is a system and method enabling the use of sludge, waste or other organic material as feed for the polychaete, either directly or pre-processed or via biological conversion.

Also provided herein is a system that is compact and space-saving.

Also provided herein is a system that is energy and resource efficient.

Also provided herein is a system that is easily scalable by including modules.

Also provided herein is a system and method designed for plain and effective feeding and harvesting.

Further details of the disclosed embodiments will appear from the following description, claims and attached drawings.

A system for high-intensity polychaete production comprises a number of units that may be divided in modules that enables an easily scalable system.

The system comprises at least one cultivation unit. The at least one cultivation unit comprises at least one inlet at a first end for supply of water, preferably seawater, and feed from a feeding unit and an outlet at a second end for discharge of water and excess feed, and at least one retrievable tray for cultivation of polychaete.

As disclosed herein, feed may be sludge/waste for direct use, such as fish farm sludge, manure or organic waste, such as food waste, garbage, etc., or other organic products/masses, such as plant materials, seaweeds, kelps, etc. The feed may also be pre-processed sludge waste, such as by water separation, hygenization, stabilization, hydrolysis or dissolving, sieving, etc.

The feed may also be sludge/waste converted to other biomass (after pre-processing), such as micro-organisms, bacteria, micro-algae, or similar, or enrichment of organic connections based on biological production, such as poly-hydroxy alkanoate, etc.

In accordance with one embodiment of the system, the cultivation unit comprises several retrievable trays arranged in series in longitudinal direction of the cultivation unit.

According to one embodiment of the system, the cultivation unit comprises several rows of retrievable trays or series of retrievable trays in height direction.

In accordance with a further embodiment of the system, the at least one tray is provided with at least one longitudinally extending dividing wall forming at least two longitudinally extending parallel compartments or chutes in the tray.

According to a further embodiment, the at least one tray is provided with fixed or exchangeable riffled bottom.

In accordance with a further embodiment of the system the at least one tray at ends thereof is provided with means to allow water and feed to flow into and out of the tray.

According to a further embodiment, the cultivation unit is formed by a housing enclosing the at least one tray or series of trays in longitudinal direction with a spacing forming an inlet chamber and an outlet chamber at respective ends of the at least one tray or series of trays.

In accordance with a further embodiment of the system, it comprises two or more cultivation units.

According to one embodiment, the system comprises at least one harvesting unit adapted for sorting polychaete ready for harvesting from minor polychaete, spatfall, eggs, water and feed.

In accordance with a further embodiment, the system comprises at least one seeding unit adapted for seeding of empty trays based on the sorted minor polychaete, spatfall and eggs as well as fresh feed.

According to a further embodiment, the system may also use one-time spawning polychaete. In such an embodiment, the polychaete is harvested before spawning and then some polychaete is transferred to a separate unit for production of spawn/spatfall that may be used in the seeding unit.

According to a further embodiment, where the polychaete is of a species that is spawning pelagically, an additional harvesting unit capable of catching eggs from discharge water from the cultivation unit is used, i.e. forming an egg collector, followed by seeding as described above.

According to a further embodiment the system comprises one or more means for subjecting the cultivated polychaete with certain temperature, certain light or certain sound, in order to influence the growth, development and composition of polychaete.

A method for high-intensity production polychaete comprises cultivating polychaete in at least one tray in at least one cultivation unit by supplying seawater and feed.

According to one embodiment, the method comprises an initial seeding of polychaete in the at least one empty tray.

In accordance with a further embodiment, it comprises retrieving polychaete ready for harvesting from the cultivation unit and separating polychaete ready for harvesting from minor polychaete, spatfall, eggs, water and feed.

In accordance with a further embodiment, it comprises seeding the separated minor polychaete, spatfall and eggs together with feed in an empty tray and insertion of the tray in the cultivation unit for new production cycle.

According to a further embodiment the method comprises performing self-pealing of the harvested polychaete.

According to a further embodiment the method comprises using one-time spawning polychaete. The method further comprises harvesting the polychaete before spawning and next transferring some of the polychaete to a separate container or similar for production of spawn/spatfall that may be used in the seeding unit, as described above.

According to a further embodiment the method comprises using polychaete species that are spawning pelagically, and catching eggs from discharge water from the cultivation unit, followed by seeding as described above.

According to a further embodiment the method comprises subjecting the cultivated polychaete with certain temperature, certain light or certain sound, in order to influence the growth, development and composition of polychaete.

According to a further embodiment, it comprises repeating the steps for all trays in a production unit.

Accordingly, after the initial seeding, the further production of the polychaete will be based on minor polychaete, spatfall, eggs, i.e. progeny of the first production. It might, however, be preferable to introduce fresh polychaete from time to time to ensure a healthy population of the polychaete.

Thus provided herein is a system and method for high-intensity polychaete production. By using several production units a continuous polychaete production may be achieved, as when harvesting polychaete from one production the other production unit(s) will continue production.

The disclosed embodiments enable the use of minor polychaete, spatfall and eggs for a new production cycle.

Further preferable features and advantageous details of the disclosed embodiments will appear from the following example description, claims and attached drawings.

BRIEF DESCRIPTION OF THE DRAWINGS

The present invention will below be described in further details with references to the attached drawings, where.

DETAILED DESCRIPTION

A system for high-intensity polychaete production according to the present invention comprises a number of units that may be divided in modules that enables an easily scalable system. The main components of the system are at least one cultivation unit 100 for cultivation of the polychaete and a feeding unit 400. The system preferably also comprises at least one harvesting unit 500 and at least one seeding unit 700.

Reference is first made to FIGS. 1A-1E showing principle drawings of a cultivation unit 100 polychaete production according to one embodiment of the system.

Figure 1A:
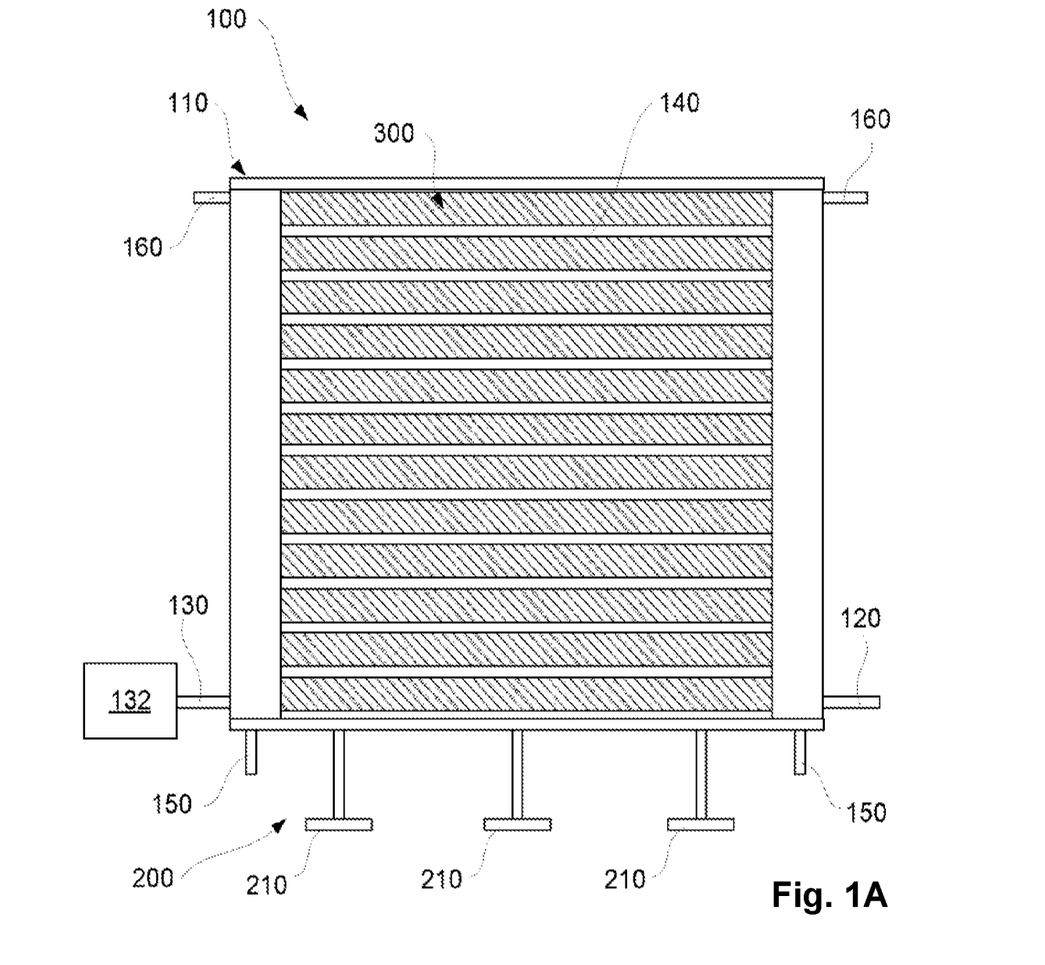
FIGS. 1A-1E are principle drawings of a cultivation unit according to the disclosed embodiments and components thereof.
Figure 1B:
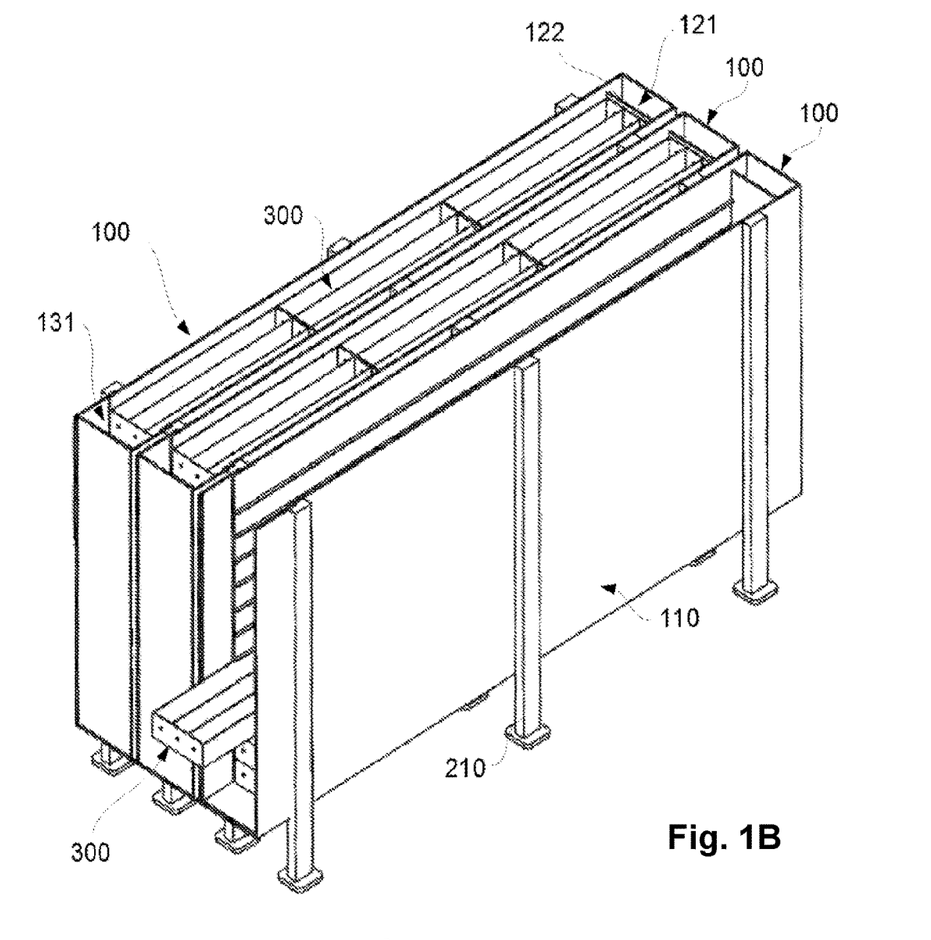

The at least one cultivation unit 100 is formed by a housing 110, in the embodiment mainly rectangular, wherein at least one end thereof is detachable or provided with a door, lid or port that may be opened to achieve access to the interior thereof. In a further embodiment, also the top side is detachable. The housing 110 may further be arranged to a support structure 200 comprising one or more legs 210.

The cultivation unit 100 comprises at least one retrievable tray 300 accommodated in the housing 110 and retrievably arranged in the housing 110. The cultivation unit 100 is further provided with at least one inlet 120 at a first end for supply of water, preferably seawater, and feed, and at least one outlet 130 at a second end for discharge of water to provide a continuous or discontinuous flow of water through cultivation unit 100, as well as discharge of excess feed.

Figure 3:
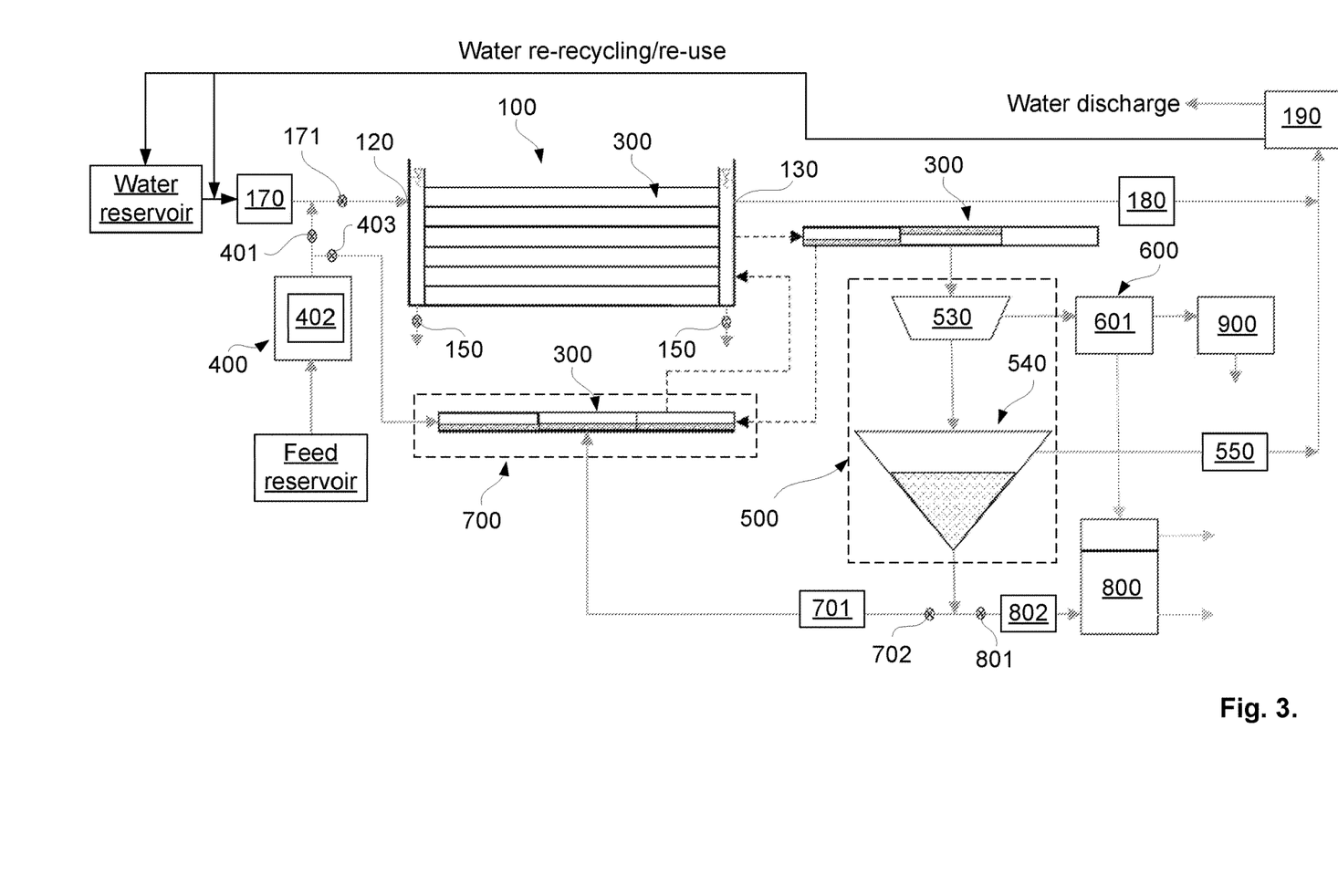
FIG. 3 is principle drawing of a system and the steps of production.

In one embodiment, the supply of water is provided by a suitable controllable pump unit 170, see FIG. 3, arranged to the inlet 120 at outlet side thereof via one or more controllable valves 171, and to a water reservoir at inlet side, preferably a seawater reservoir. The outlet 130 of the at least one cultivation unit 100 will further typically be arranged to inlet side of a controllable pump 180 for the discharge of water and excess feed, which controllable pump 180 at outlet side typically will be arranged to a water treatment unit/system 190 at the outlet side thereof, which water treatment unit/system 190 is adapted for processing the discharged water for re-use and water discharge to the environments, as shown in FIG. 3. The discharged water from the treatment unit/system 190 for re-use is supplied to the water reservoir or directly to the mentioned pump unit 170, in this way providing recycling of water. This will reduce the water consumption and thus also the environmental footprint.

The mentioned detachable or openable side or door, lid or port of the at least one cultivation unit 100 is preferably arranged at the outlet side of the housing 110.

The housing 110 encloses the at least one tray 300 with a spacing, at least at the ends thereof, providing an inlet chamber 121 in fluid communication with the inlet 120 and an outlet chamber 131 in fluid communication with the outlet 130. According to one embodiment, the inlet chamber 121 is formed in the housing 110 by a vertically extending wall 122, which also will act as a stopper for the at least one tray 300 in the cultivation unit 100. In an alternative embodiment the vertically extending wall 122 is replaced with vertically extending beams at each side of the housing 110 acting as stoppers for the at least one tray 300. In yet a further alternative embodiment the mentioned guides or rails 140 at rear end, i.e. the end facing the inlet chamber 121, is provided with at least one vertically extending member acting as a stopper for the at least one tray. According to one embodiment, the mentioned inlet 120 and outlet 130 are arranged at lower part of the housing 110. The arrangement of the inlet 120 at lower part will be favourable as regards avoiding sedimentation of feed in the inlet chamber 121 and thus ensure that the sedimentation of the feed is performed in the mentioned at least one tray 300.

The housing 110 is further provided with pairs of longitudinal guides or rails 140 for arrangement of the mentioned at least one retrievable tray 300 in the housing 110. The retrievable tray 300 is in the shown embodiment mainly rectangular and has a shape and size adapted the interior of the housing for accommodation therein and movable on the mentioned guides or rails 140.

According to one embodiment, the housing 110 is adapted to accommodate a number of retrievable trays 300 in height direction thereof, as well as in longitudinal direction, as will be further described below.

In the embodiment shown in FIG. 1B, the cultivation unit 100 comprises several trays 300 arranged in series in longitudinal direction, in the shown embodiment three trays 300 in series, and several trays 300 arranged in rows in height direction, in the shown embodiment twelve rows of trays in height direction.

Figure 1C:
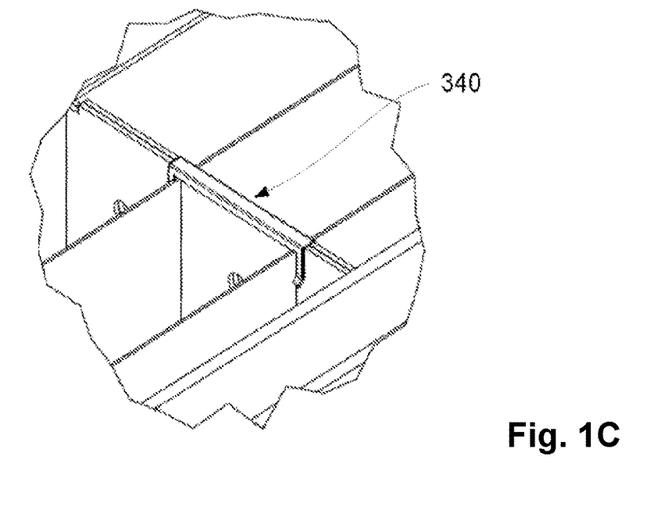
Figure 1D:
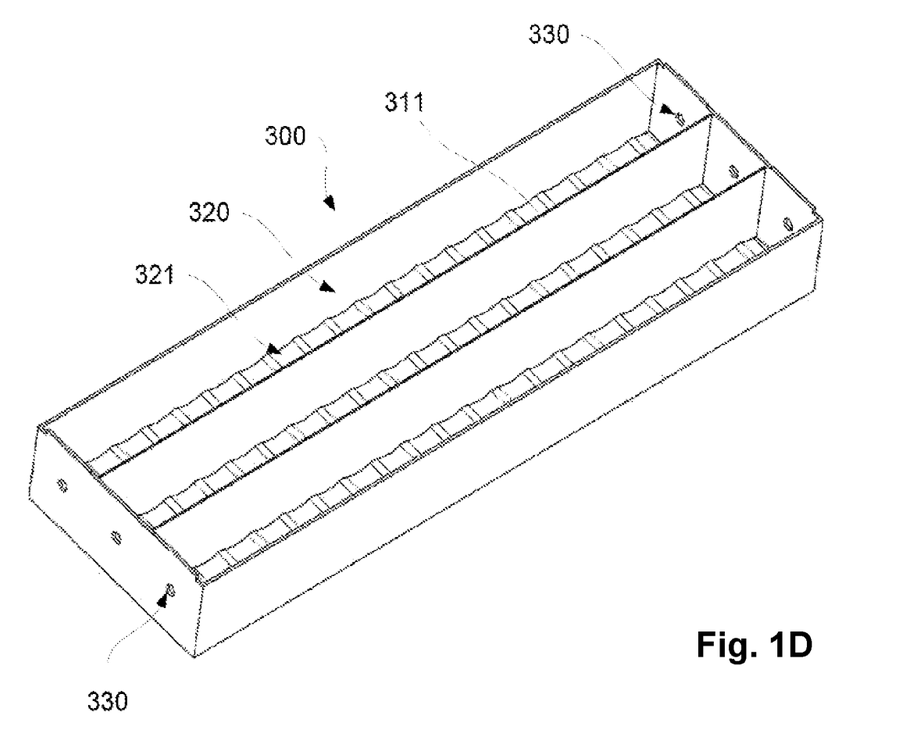
Figure 1E:
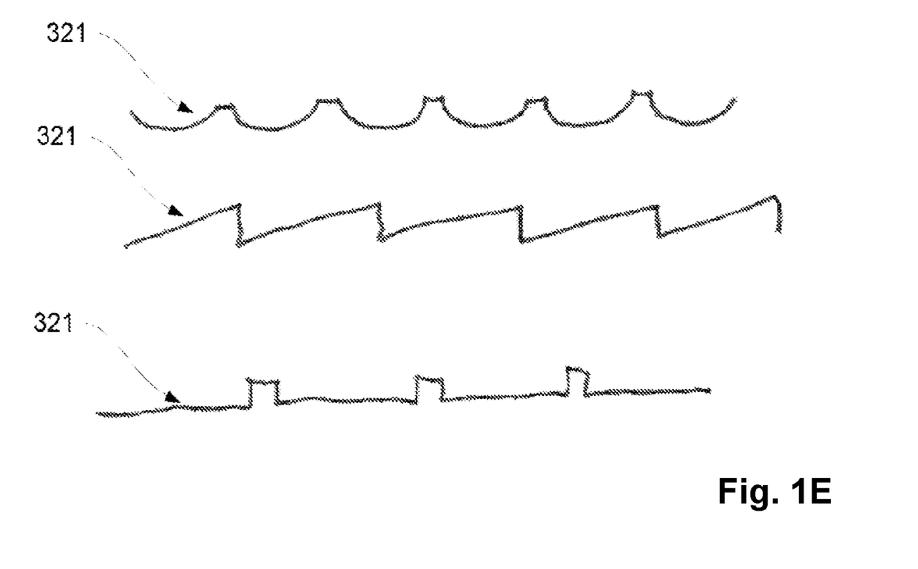

According to a further embodiment of the at least one retrievable tray 300, the at least one retrievable tray 300 is provided with at least one longitudinally extending dividing wall 311, as shown in FIG. 1D, forming at least two longitudinally extending parallel compartments or chutes 320 in the mentioned retrievable tray 300. In the shown embodiment, there are two longitudinally extending parallel dividing walls 311, spaced apart such that the interior of the retrievable tray 300 is divided into three longitudinally extending compartments or chutes 320.

According to a further embodiment of the system, the retrievable tray 300 is further provided with a riffled bottom 321. In the shown embodiment in the mentioned longitudinally extending compartments or chutes 320. The riffled bottom 321 may be a fixed or exchangeable, which riffled bottom 321 is adapted the polychaete to be cultivated. By using an exchangeable riffled bottom 321, the profile of the riffled bottom 321 may be exchanged according to the desires of the user as well as adapted to the polychaete to be cultivated. Different profiles of the riffled bottom 321 with different cross-section, such as V-shaped, square, triangle, etc., as e.g. shown in FIG. 1E may be used. The mentioned riffles extend in transversal direction of the bottom with an elevation forming recesses therebetween for cultivation of the polychaete.

The mentioned retrievable tray 300 is further provided with means 330 to allow water and feed to flow into and out of the retrievable tray 300, when inserted into the cultivation unit 100. By this, water and feed may flow from one tray 300 to an adjoining tray 300 when several trays 300 are arranged in series, as well as allow flow from the inlet chamber 121 to the adjoining tray 300 and to the outlet chamber 131 from the adjoining tray 300. In the shown embodiment, this feature means 330 are formed by holes or openings 330, preferably at upper part of the end walls of the retrievable tray 300. The mentioned holes or openings 330 will, when the tray 300 is provided with several parallel compartments or chutes 320 be arranged in fluid communication with the respective compartments or chutes 320, allowing flow into and out of the trays 300. In an alternative embodiment, the end walls of the trays 300 are provided with recesses allowing flow into and out of the trays 300. Other alternatives will be obvious for a skilled person.

In connection with the mentioned holes or openings 330 there are preferably arranged corresponding sealing means or joints (male/female) (not shown) to provide a watertight connection of trays 300 arranged in series.

The mentioned vertically extending wall 122 of the inlet chamber 121 will further be provided with holes or openings (not shown) adapted the holes or openings 330 in the trays 300 arranged in the housing 110 for allowing fluid communication between the inlet chamber 121 and the ends of the trays 300 facing the inlet chamber 121.

It will further be preferable to arrange locking means 340, as e.g. shown in FIG. 1C, in the form of a clip 340 arranged over facing ends of two trays 310 arranged in series in longitudinal direction of the housing 110, wherein the clip 340 retains/locks two trays 300 arranged in series to each other. The clip 340 is easily detachable when the mentioned trays 300 are to be separated. Other means for retaining two trays 300 together will be obvious for a skilled person.

The mentioned retrievable trays 300 are easily insertable and retrievable from the housing 110 via the mentioned longitudinal guides or rails 140, as shown in FIG. 1B, via the detachable or openable side or door, lid or port at the outlet side of the housing 110. The mentioned locking means 340 ensures that all the trays 300 arranged in series will be easily retrieved from the cultivation unit 100 by pulling the first tray 300 in a series.

As shown in FIGS. 1A and 1B the cultivation unit 100 may comprise several rows of at least one tray 300. In the shown embodiments, there are three trays 300 arranged in series per row in the cultivation unit 100. The shown cultivation units 100 is further adapted for twelve rows of trays 300 in height direction, giving a total number of 108 trays for each cultivation unit 100.

The housing 110 thus form a container or tank for the trays 300, and wherein the trays 300 are arranged such that it is formed a "dam" between the inlet chamber 121 and outlet chamber 131. The difference in supplied water level (water and sludge) between the inlet chamber 121 and outlet chamber 131 is the hydraulic driving force through the compartments or chutes 320 in the trays 300.

According to a further embodiment, the inlet chamber 121 is provided with a sealed top such that it may be pressurized for a more rapid flow of water and feed through the chambers or chutes 320 of the trays 300, especially at an initial stage.

In the latter sealed embodiment, one is not dependent on the level difference as the entire cultivation unit 100 is pressurized by the mentioned pump unit 170 providing the required hydraulic driving force through the compartments or chutes 320 in the trays 300.

In accordance with a further embodiment, the inlet chamber 121 and outlet chamber 131, respectively, are provided with bottom valves 150 for drainage for rapid drainage when the cultivated polychaete is to be harvested, as well as for maintenance or cleaning.

According to a further embodiment, the outlet chamber 131 and inlet chamber 121 are provided with an overflow 160 to avoid possible damage of the cultivation unit 100 and/or spill in the case of failure in control of the fluid level in the ensure desired water level in the cultivation unit 100.

According to a further embodiment, the outlet 130 is arranged to a device 132 for hydraulic controlling (adjusting) of the fluid level in the cultivation unit 100. E.g., this device 132 is at least one controllable valve or an overflow device (box).

The mentioned cultivation unit 100 may be arranged as a module in a larger system, wherein a number of such cultivation units 100 are arranged to a common support structure 200 such that a module-based system is achieved. Where several such modules/cultivation units 100 are arranged to each other, the inlet 120 and outlet 130 of each of the cultivation units 100 may be arranged to an inlet manifold and outlet manifold separately controlling the inlet and outlet of the cultivation units 100. Of course, separate inlets and outlets may be used, but the use of manifolds will be space saving.

The polychaete to be cultivated is feed with sludge, such as fish farm sludge or other types of sludge or waste, alternatively other kinds of feed or organic particles or material may be used, as discussed above.

The system comprises at least one feeding unit 400 for supplying feed to the cultivation unit 100. The feed may be supplied to the cultivation unit 100 directly via a dedicated inlet in the cultivation unit 100 or via the water flow from the water pump unit 170 via one or more controllable valves 401.

The feeding unit 400 is adapted for feed treatment, i.e. sludge treatment in the shown embodiment, and comprises at least one controllable pump 402 for supplying feed to the water flow or directly to the cultivation unit 100, to at least one tray 300 via at least one dedicated inlet (not shown) in the cultivation unit 100. The feeding unit 400 is provided with feed from a feed reservoir.

The feeding unit 400 is adapted to supply feed according to desired feeding regime, e.g. at a high or low frequency, continuously, discontinuously, high or low concentration, etc.

In the case where the feed is supplied to the water flow, one may, e.g., increase the water flow to ease/facilitate the transport of the feed to the cultivation unit 100, and next stop the water flow for allowing the feed to sediment in the cultivation unit 100. E.g. feed with different % dry matter may be used, such as from 1% to approximately 50% dry matter.

The cultivation unit 100 is according to a further embodiment of the system provided with one or more sensors or sensor systems for controlling the cultivation of the polychaete. Examples of such systems are temperature, light, weight, flow sensor, water content, feed access, flow sensor, turbidity, oxygen content, flow velocity, etc., wherein one or more of these may be arranged both at the inlet and outlet to monitor the cultivation, and thus be used for controlling the at least one feeding unit 400, as well as the supply of water. The sensors or sensor system may also be used for indicating when the cultivated polychaete is ready for harvesting.

The cultivation unit 100 is according to a further embodiment of the system comprising one or more means or systems for subjecting the cultivated polychaete with certain temperature, certain light or certain sound, in order to influence the growth, development and composition of polychaete.

The cultivation unit 100 is according to a further embodiment provided with means for changing/adjusting the interior flow with regard to sedimentation.

According to a further embodiment of the cultivation unit 100 it is provided with means for additional supply of water and/or light.

Figure 2:
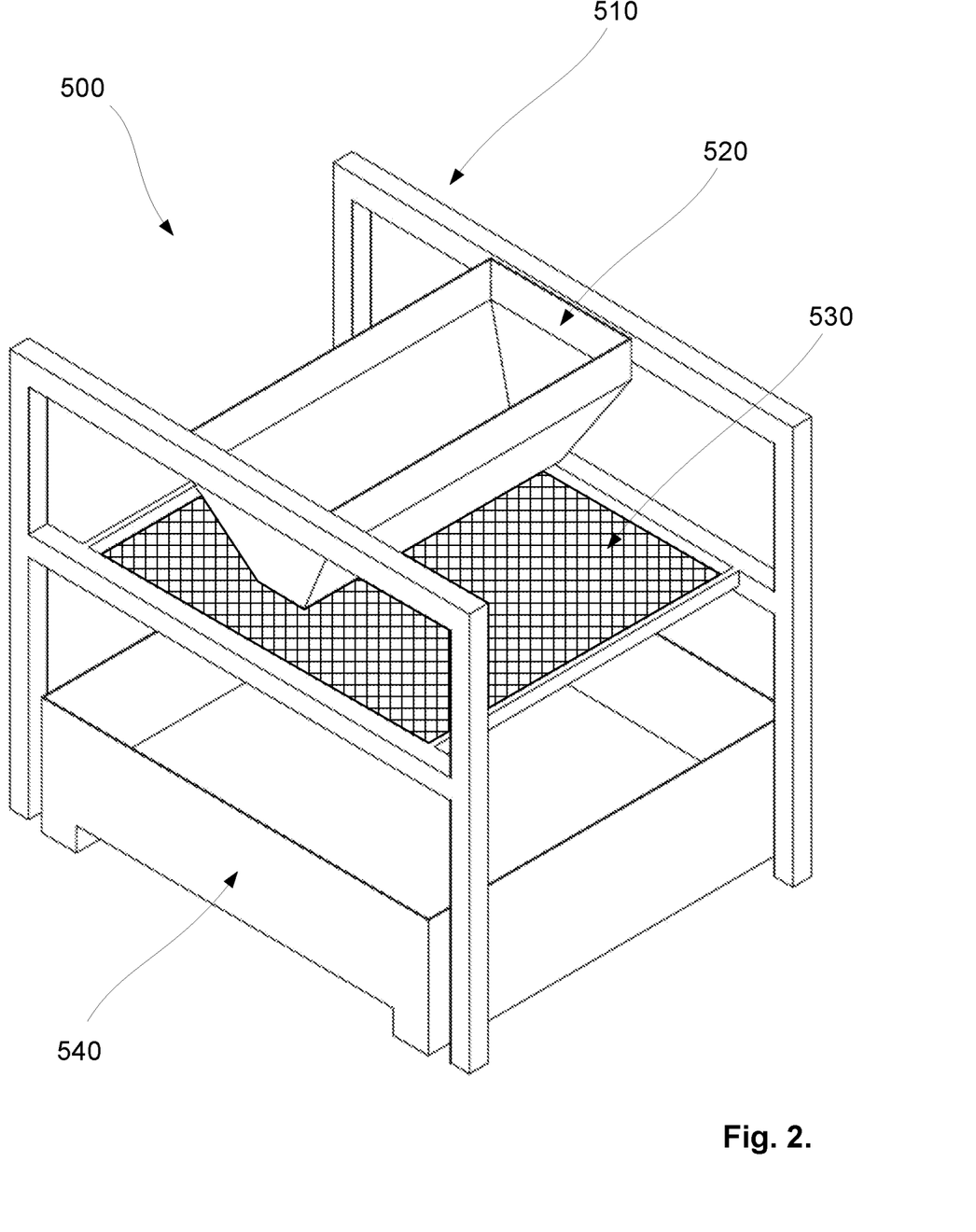
FIG. 2 is a principle drawing of an example of a harvesting unit.

Reference is now made to FIG. 2 which is a principle drawing of an example of a harvesting unit 500. The harvesting unit 500 according to the example comprises a support structure 510 for arrangement of a funnel 520, screen or sieve unit 530 and sedimentation tank or container 540. The funnel 520 is arranged at an uppermost position in the support structure 510 wherein material (water, sludge, cultivated polychaete) from a tray 300 retrieved from the cultivation unit 100 is emptied when the polychaete is ready for harvesting. The screen or sieve unit 530 is arranged under the funnel 520, which screen or sieve unit 530 is adapted to sort out polychaete ready for harvesting from remaining material (water, sludge, cultivated polychaete that is not ready for harvesting (minor polychaete, spatfall, eggs)). The screen or sieve unit 530 is for this provided with a mesh size adapted for stopping polychaete with a size ready for harvesting, while letting all other material (minor polychaete, spatfall, eggs, water, feed (sludge)) through.

Under the screen or sieve unit 530 is the sedimentation tank or container 540 arranged, which is provided with an open side facing the screen or sieve unit 530 for receiving the mentioned material that is not sorted out by the screen or sieve 530.

The separated polychaete ready for harvesting that is sorted out by the screen or sieve unit 530 is next transferred to a self-pealing unit 600.

Sludge, minor polychaete, spatfall and eggs are separated from the water in the sedimentation tank or container 540 by removing the water, e.g., by means of a controllable pump 550 connected at inlet side thereof to upper part of the sedimentation tank or container 540 and at outlet side thereof to the water treatment unit/system 190. Excess sludge (some of the sludge) with minor polychaete, spatfall, eggs is removed from the sedimentation tank or container 540 and transferred to a seeding unit 700, see FIG. 3, e.g. by using a controllable pump 701 connected to an outlet at lower part of the sedimentation tank or container 540 via one or more controllable valves 702.

The remaining water and rest of the sludge is removed from the sedimentation tank or container 540 and discharged to a waste outlet or a bio-residual treatment unit/system 800 connected to the sedimentation tank or container 540 via one or more controllable vales 801 and pump 802.

The seeding unit 700 is further connected to the feeding unit 400 via one or more controllable valves 403 for supply of feed to the seeding unit 700. In the seeding unit 700, empty trays 300 are prepared for a new production cycle in the cultivation unit 100. By seeding/distributing excess sludge with minor polychaete, spatfall and eggs in the empty trays 300 together with new fresh feed, in the shown embodiment sludge, this ensures a new generation of polychaete that may be cultivated in the cultivation by reinserting the filled trays 300 into the cultivation unit 100 for a new production cycle.

The mentioned self-pealing unit 600 is according to one embodiment formed by a tank or container 601 wherein harvested polychaete is processed. The tank or container 601 is provided with means or connected to means for adjustment/manipulation of water quality to different qualities, such as, but not limited to, the use of chemicals and/or gas. Desired quality will be dependent on which species of polychaete and which result to be achieved. For *Capitella Capitata*, one e.g. adjusts water quality by lowering the oxygen content such that the polychaete lets go of the bursa (slime bag), and the polychaete can next be transferred to a polychaete pre-processing unit 900 for processing to with the purpose of constituting an ingredient in fish feed or for other use. The remains in the self-pealing unit 600 may be transferred to the bio-residual treatment unit/system 800 for further processing.

Reference is now made to FIG. 3 which is principle drawing of the disclosed system. The figure also shows the flow of feed, water and polychaete in the system and the processes thereof. The polychaete production will now be described.

After an initial seeding of polychaete in the trays 300, the trays 300 are inserted into the cultivation unit 100 for cultivation. The cultivation of the polychaete in the cultivation unit 100 is performed by supplying of water and feed over a desired production cycle. Depending on which species that are grown, it may typically take approximately two months before the polychaete is ready for harvesting.

When the polychaete is ready for harvesting, the supply of water and feed to the cultivation unit 100 is stopped, and the cultivation unit 100 is drained. The trays 300 are next retrieved from the cultivation unit 100 and disconnected from each other, if arranged in series. By means of transport means, such as a truck 950, manipulator system or similar systems capable of moving the retrieved trays 300, the retrievable trays 300 are transported to the harvesting unit 500, where the content of the retrieved trays 300 are emptied into the harvesting unit 500.

Figure 4A:
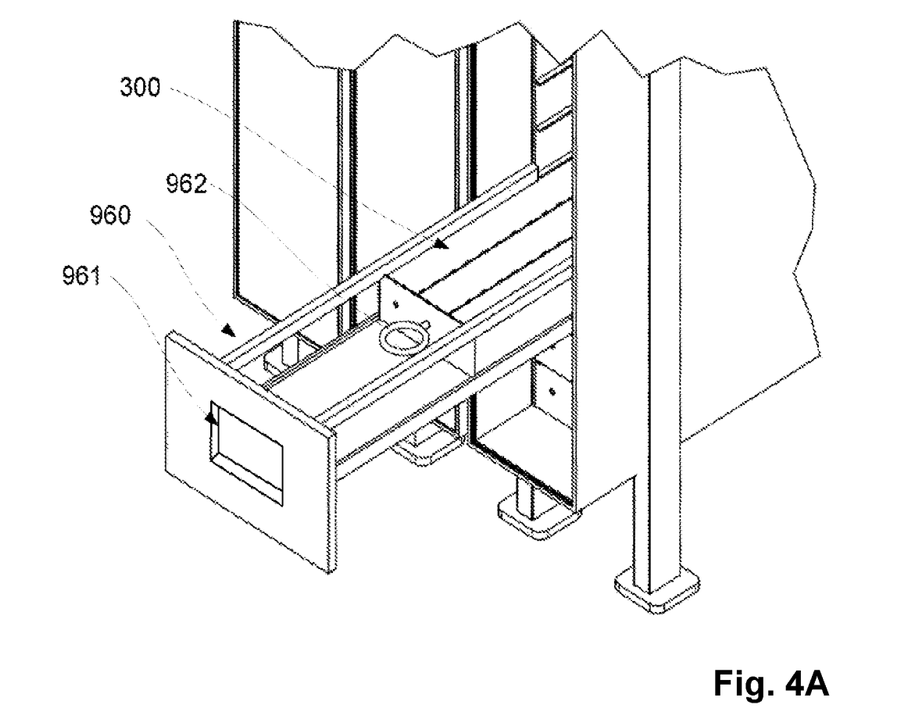
FIGS. 4A-4C are principle drawings of handling of a tray for harvesting of cultivated polychaete.
Figure 4B:
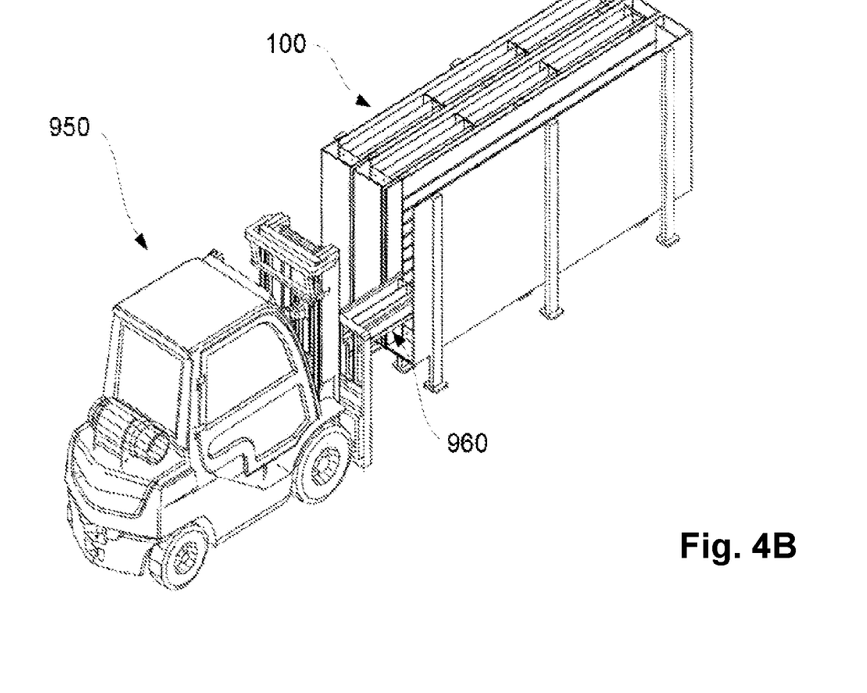
Figure 4C:
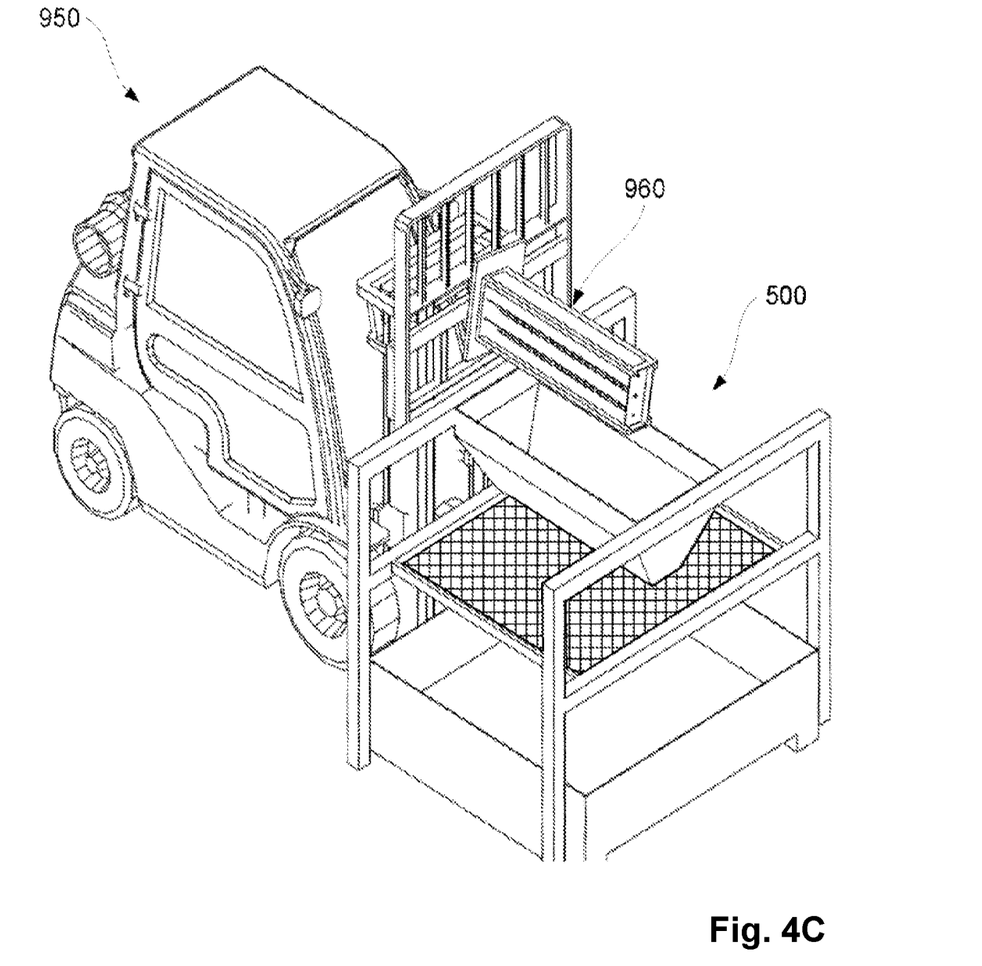

Reference is now made to FIGS. 4A-4C showing principle drawings of the retrieval process and transport process to the harvesting unit 500 and also for transport to the seeding unit 700 after emptying at the harvesting unit 500. For handling the mentioned trays 300 it will be preferable to use a handling unit 960 adapted for receiving the mentioned tray 300 and provided with locking means to secure the tray 300 to the handling unit 960. The handling unit 960 is further preferably adapted with an opening 961 to allow access to the tray 300 to be handled, such that one may insert an adapted tool (not shown), such as a winch wire or manipulator arm, for engaging the tray 300 to be handled, and thus withdraw the tray 300 from the housing 110 and into the handling unit 960. In one embodiment, the tray 300 may be provided with a hook 962 for simple engagement by the adapted tool.

An example of the use of a truck 950 is shown in FIGS. 4B and 4C, where the mentioned handling unit 960 is arranged to the truck 950. In FIG. 4B is shown a principle drawing of where the truck 950 via the handling unit 960 retrieves a tray 300 from a cultivation unit 100 and in FIG. 4C is shown a principle drawing where the truck 950 by means of a rotational movement of the handling unit 960 with the tray 300 empties the content of the tray 300 into the harvesting unit 500 before moving the emptied tray to the seeding unit 700.

The polychaete ready for harvesting is sorted out in the harvesting unit 500, as described above, and the remaining content of minor polychaete, spatfall and eggs, as well as some of the feed (sludge) after a sedimentation is transferred to the seeding unit 700, wherein the emptied trays 300 are seeded with the mentioned minor polychaete, spatfall and eggs together with fresh/new feed (sludge) from the feeding unit 400 and the trays 300 are again ready for entering the cultivation unit 100 for a new production cycle.

For an embodiment with species of polychaete that is spawning pelagically, i.e. laying eggs in the fluid flow, an additional harvesting unit (not shown) is arranged to the outlet 130 of the cultivation unit 100, wherein the additional harvesting unit is adapted for catching eggs in discharge water thereof, i.e. forming an egg collector.

According to a further embodiment, it comprises a separate container (not shown) or similar for production of spawn/spatfall prior to seeding by means of the seeding unit 700.

The system according to a further embodiment comprises one or more units for converting sludge or waste to biomass/bacteria for use as feed for the polychaete.

According to a further embodiment, the species of polychaete cultivated is one cultivating on hard surfaces and which go into the water masses in the cultivation unit 100 for feed. In such a case, the bottom of the trays 300 may be adapted the relevant species. In such a case, only a low amount of sludge/waste is required in the mentioned trays 300 and wherein the feeding is adapted in the supply of fluid to the cultivation unit 100, i.e. the fluid flow through the cultivation unit 100.

An advantage with having several cultivation units 100 as modules in the system is that by performing an initial seeding and start of cultivation at different starting time, a continuous polychaete production is achieved due to that the polychaete in the different cultivation units 100 will be ready for harvesting at different time, such that the remaining cultivation units 100 will continue production while one of the cultivation units 100 is harvested.

Accordingly, the disclosed embodiments provide a system for industrialization of continuous polychaete production, especially for the use of polychaete as a content in fish feed, but the polychaete may also have other areas of use, such as an ingredient in feed for agriculture farming, feed for domestic animals, aquarium fish, bait, angling, and cosmetics or similar.

The described embodiments of the system and components thereof further has low space requirements.

The disclosure further provides a system where feeding and harvesting is simple and effective, and which is easily scalable by adding additional units/components of the system.

The invention claimed is:

1. A system for high-intensity polychaete production, comprising:
   at least two cultivation units;
   a feeding unit;
   each said cultivation unit being formed by a housing provided with:
      at least one inlet at a first end thereof for supply of water and feed from the feeding unit; and
      an outlet at a second end thereof for discharge of water and excess feed;
   at least one of the at least two cultivation units comprising rows of trays arranged along a height direction of the housing, said trays being horizontally retrievable from the housing;
   each said row of trays comprises several trays arranged in series in a longitudinal direction of the cultivation unit;
   the housing enclosing, in said longitudinal direction, the series of trays arranged in a horizontal plane, with a spacing forming an inlet chamber and an outlet chamber at respective ends of the series of trays, with the inlet chamber being in fluid communication with the inlet and with the outlet chamber being in fluid communication with the outlet,
   wherein each of the trays include holes or recesses located at ends thereof with the holes or recesses being configured to allow water and feed to flow into and out of each of the trays.

2. The system according to claim 1, wherein at least one of said trays includes at least one longitudinally extending dividing wall forming at least two longitudinally extending parallel compartments or chutes.

3. The system according to claim 2, wherein said at least one tray includes a fixed or exchangeable riffled bottom.

4. The system according to claim 1, wherein at least one of said trays includes a fixed or exchangeable riffled bottom.

5. The system according to claim 1, further comprising at least one harvesting unit adapted for sorting polychaete ready for harvesting from minor polychaete, spatfall, eggs, water and feed.

6. The system according to claim 5, further comprising at least one seeding unit adapted for seeding of the trays when empty.

7. The system according to claim 6, further comprising one or more separate units for production of spawn or spatfall that are usable in the seeding unit.

8. The system according to claim 1, further comprising at least one self-pealing unit.

9. The system according to claim 1, further comprising a harvesting unit arranged at the outlet, the harvesting unit being adapted for catching eggs in discharge water thereof.

10. The system according to claim 1, wherein the system is adapted to utilize one or more converting units that are configured to convert sludge or waste to biomass or bacteria for use as feed for the polychaete.

11. The system according to claim 1, the system is adapted to utilize one or more influencing units configured to subject the polychaete to certain temperature, light or certain sound, in order to influence growth, development and composition of the polychaete.

12. A method for high-intensity polychaete production using the system according to claim 1, the method comprising:
    cultivating the polychaete in said trays by supplying seawater and feed to the inlet from the feeding unit and discharging water and excess feed from the outlet.

13. The method according to claim 12, further comprising providing an initial seeding of the polychaete in at least one empty tray.

14. The method according to claim 12, further comprising retrieving the polychaete ready for harvesting from at least one of the at least two cultivation units and separating polychaete ready for harvesting from minor polychaete, spatfall, eggs, water and feed.

15. The method according to claim 14, further comprising seeding the separated minor polychaete, spatfall and eggs together with feed in an empty tray and inserting a respective tray for a new production cycle.

16. The method according to claim 15, further comprising harvesting the polychaete before spawning and then transferring some of the polychaete to a separate unit for production of spawn or spatfall before seeding in an empty tray.

17. The method according to claim 14, further comprising performing self-pealing of the polychaete when harvested.

18. The method according to claim 12, further comprising using one or both of one-time spawning polychaete or species that are spawning pelagically.

19. The method according to claim 12, further comprising utilizing polychaete spawning pelagically, and catching eggs from discharge water from one of the cultivation units, followed by seeding.

20. The method according to claim 12, the method is utilized with a system adapted to subject cultivated polychaete to certain temperature, light or sound, in order to influence growth, development and composition of the polychaete.

* * * * *